US010813560B2

(12) United States Patent
Tan et al.

(10) Patent No.: US 10,813,560 B2
(45) Date of Patent: *Oct. 27, 2020

(54) DEFIBRILLATOR CHARGING

(71) Applicant: Zoll Medical Corporation, Chelmsford, MA (US)

(72) Inventors: Qing Tan, Somerville, MA (US); Gary A. Freeman, Waltham, MA (US); Frederick J. Geheb, Danvers, MA (US); Martin E. Bures, Somerville, MA (US); Annemarie Silver, Bedford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 81 days.

This patent is subject to a terminal disclaimer.

(21) Appl. No.: 16/174,981

(22) Filed: Oct. 30, 2018

(65) Prior Publication Data

US 2019/0059745 A1    Feb. 28, 2019

Related U.S. Application Data

(63) Continuation of application No. 15/091,694, filed on Apr. 6, 2016, now Pat. No. 10,143,387, which is a
(Continued)

(51) Int. Cl.
*A61B 5/0205* (2006.01)
*G09B 23/28* (2006.01)
(Continued)

(52) U.S. Cl.
CPC ............ *A61B 5/0205* (2013.01); *A61B 5/044* (2013.01); *A61B 5/11* (2013.01); *A61B 5/14542* (2013.01); *A61B 5/7282* (2013.01); *A61B 5/742* (2013.01); *A61B 5/746* (2013.01); *A61H 31/005* (2013.01); *A61N 1/046* (2013.01); *A61N 1/0492* (2013.01); *A61N 1/3925* (2013.01); *A61N 1/3931* (2013.01); *A61N 1/3975* (2013.01); *A61N 1/3987* (2013.01); *A61N 1/3993* (2013.01);
(Continued)

(58) Field of Classification Search
CPC ............................ A61N 1/3981; A61N 1/3975
See application file for complete search history.

(56) References Cited

U.S. PATENT DOCUMENTS 4,198,963 A    4/1980  Barkalow et al.
4,326,507 A    4/1982  Barkalow
(Continued)

FOREIGN PATENT DOCUMENTS

EP    1595575 A2    11/2005
EP    1834622 A2     9/2007
(Continued)

OTHER PUBLICATIONS

Aase et al., "CPR Artifact Removal from Human ECG Using Optimal Multichannel Filtering," IEEE Transactions on Biomedical Engineering, (2000), pp. 1440-1449, vol. 47(11).
(Continued)

*Primary Examiner* — Joseph M Dietrich
(74) *Attorney, Agent, or Firm* — The Webb Law Firm

(57) ABSTRACT

Systems and methods related to the field of cardiac resuscitation, and in particular to devices for assisting rescuers in performing cardio-pulmonary resuscitation (CPR).

31 Claims, 9 Drawing Sheets

FIG. 2

Related U.S. Application Data continuation of application No. 13/025,327, filed on Feb. 11, 2011, now abandoned.

(60) Provisional application No. 61/307,690, filed on Feb. 24, 2010, provisional application No. 61/304,119, filed on Feb. 12, 2010.

(51) Int. Cl.

| | | |
|---|---|---|
| *A61H 31/00* | (2006.01) | |
| *A61N 1/39* | (2006.01) | |
| *G06F 19/00* | (2018.01) | |
| *G09B 19/00* | (2006.01) | |
| *G16H 40/63* | (2018.01) | |
| *A61B 5/044* | (2006.01) | |
| *A61B 5/11* | (2006.01) | |
| *A61B 5/145* | (2006.01) | |
| *A61B 5/00* | (2006.01) | |
| *A61N 1/04* | (2006.01) | |
| *G16H 20/40* | (2018.01) | |
| *G16H 50/00* | (2018.01) | |
| *A61B 5/083* | (2006.01) | |
| *A61B 5/0402* | (2006.01) | |
| *A61B 5/08* | (2006.01) | |
| *A61B 5/0408* | (2006.01) | |

(52) U.S. Cl.
CPC .......... *G06F 19/00* (2013.01); *G06F 19/3481* (2013.01); *G09B 19/003* (2013.01); *G09B 23/288* (2013.01); *G16H 20/40* (2018.01); *G16H 40/63* (2018.01); *G16H 50/00* (2018.01); *A61B 5/0402* (2013.01); *A61B 5/0408* (2013.01); *A61B 5/082* (2013.01); *A61B 5/0836* (2013.01); *A61B 2562/0219* (2013.01); *A61H 2201/5076* (2013.01); *A61H 2201/5084* (2013.01); *A61H 2230/04* (2013.01); *A61H 2230/205* (2013.01); *A61H 2230/207* (2013.01); *A61H 2230/30* (2013.01); *A61N 1/3937* (2013.01); *A61N 1/3981* (2013.01)

(56) References Cited

U.S. PATENT DOCUMENTS

| 4,397,306 A | 8/1983 | Weisfeldt et al. |
|---|---|---|
| 5,020,516 A | 6/1991 | Biondi et al. |
| 5,377,671 A | 1/1995 | Biondi et al. |
| 5,490,820 A | 2/1996 | Schock et al. |
| 5,683,424 A | 11/1997 | Brown et al. |
| 5,818,132 A | 10/1998 | Konotchick |
| 5,957,856 A | 9/1999 | Weil et al. |
| 6,179,793 B1 | 1/2001 | Rothman et al. |
| 6,213,960 B1 | 4/2001 | Sherman et al. |
| 6,269,267 B1 | 7/2001 | Bardy et al. |
| 6,312,399 B1 | 11/2001 | Lurie et al. |
| 6,360,125 B1 | 3/2002 | Weil et al. |
| 6,390,996 B1 | 5/2002 | Halperin et al. |
| 6,807,442 B1 | 10/2004 | Myklebust et al. |
| 7,118,542 B2 | 10/2006 | Palazzolo et al. |
| 7,220,235 B2 | 5/2007 | Geheb et al. |
| 7,242,979 B1 | 7/2007 | Kelly et al. |
| 7,272,441 B1 | 9/2007 | Chapman et al. |
| 7,565,194 B2 | 7/2009 | Tan et al. |
| 7,650,181 B2 | 1/2010 | Freeman et al. |
| 7,774,060 B2 | 8/2010 | Westenskow et al. |
| 7,993,290 B2 | 8/2011 | Lund et al. |
| 8,105,249 B2 | 1/2012 | Freeman |
| 8,204,589 B2 | 6/2012 | Freeman |
| 8,321,011 B2 | 11/2012 | Parascandola et al. |
| 8,478,401 B2 | 7/2013 | Freeman |
| 8,634,937 B2 | 1/2014 | Elghazzawi et al. |
| 8,725,253 B2 | 5/2014 | Johnson et al. |
| 8,880,166 B2 | 11/2014 | Tan et al. |
| 2002/0133197 A1 | 9/2002 | Snyder et al. |
| 2003/0144699 A1 | 7/2003 | Freeman |
| 2004/0039419 A1 | 2/2004 | Stickney et al. |
| 2004/0082888 A1 | 4/2004 | Palazzolo et al. |
| 2004/0162585 A1 | 8/2004 | Elghazzawi et al. |
| 2004/0162587 A1 | 8/2004 | Hampton et al. |
| 2004/0215112 A1 | 10/2004 | Mollenauer et al. |
| 2004/0230140 A1 | 11/2004 | Steen |
| 2004/0267325 A1 | 12/2004 | Geheb et al. |
| 2005/0085799 A1 | 4/2005 | Luria et al. |
| 2005/0101889 A1 | 5/2005 | Freeman et al. |
| 2005/0256415 A1 | 11/2005 | Tan et al. |
| 2005/0273023 A1 | 12/2005 | Bystrom et al. |
| 2006/0058848 A1 | 3/2006 | Piraino et al. |
| 2006/0089574 A1 | 4/2006 | Paradis |
| 2006/0129191 A1 | 6/2006 | Sullivan et al. |
| 2006/0173501 A1 | 8/2006 | Stickney et al. |
| 2006/0270952 A1 | 11/2006 | Freeman et al. |
| 2007/0060785 A1 | 3/2007 | Freeman et al. |
| 2007/0213775 A1 | 9/2007 | Snyder |
| 2007/0219588 A1 | 9/2007 | Freeman |
| 2008/0015645 A1 | 1/2008 | Kelly et al. |
| 2008/0027338 A1 | 1/2008 | Lu et al. |
| 2009/0024175 A1 | 1/2009 | Freeman |
| 2009/0054743 A1 | 2/2009 | Stewart |
| 2010/0049266 A1 | 2/2010 | Ochs et al. |
| 2010/0211127 A1 | 8/2010 | Eerden |
| 2010/0222718 A1 | 9/2010 | Freeman et al. |
| 2011/0040217 A1 | 2/2011 | Centen |
| 2011/0082510 A1 | 4/2011 | Sullivan |
| 2011/0117529 A1 | 5/2011 | Barash et al. |
| 2011/0172550 A1 | 7/2011 | Martin et al. |
| 2011/0202100 A1 | 8/2011 | Tan et al. |
| 2011/0202101 A1 | 8/2011 | Tan et al. |
| 2012/0226178 A1 | 9/2012 | Freeman et al. |
| 2014/0213941 A1 | 7/2014 | Johnson et al. |

FOREIGN PATENT DOCUMENTS

| JP | 2005046609 A | 2/2005 |
|---|---|---|
| JP | 2005515009 A | 5/2005 |
| JP | 2005339533 A | 12/2005 |
| JP | 2006503659 A | 2/2006 |
| JP | 2007512043 A | 5/2007 |
| JP | 2009507609 A | 2/2009 |
| JP | 200945485 A | 3/2009 |
| WO | 96028129 A1 | 9/1996 |
| WO | 02072197 A2 | 9/2002 |
| WO | 2004058351 A1 | 7/2004 |
| WO | 2005043303 A2 | 5/2005 |
| WO | 2005043306 A2 | 5/2005 |
| WO | 2006104977 A2 | 10/2006 |
| WO | 2009037621 A2 | 3/2009 |

OTHER PUBLICATIONS

American Heart Association Guidelines for CPR and ECC Highlights, Oct. 10, 2010.

Barash et al., "Novel Technology to Limit Chest Compression Interruption with Experienced Advanced Life Support Providers," American Heart Association Abstract P65, Circulation 2009, 120:S1455.

Highlights of the 2010 American Heart Association Guidelines for CPR and ECC, (Nov. 2, 2010).

Li et al., "Identifying potentially shockable rhythms without interrupting cardiopulmonary resuscitation," Crit Care Med, (2008), pp. 198-203, vol. 36(1).

Lloyd et al., "Hands-On Defibrillation: An Analysis of Electrical Current Flow Through Rescuers in Direct Contact With Patients During Biphasic External Defibrillation," Journal of the American Heart Association Circulation, (2008), pp. 2510-2514, vol. 117.

Povoas and Bisera, "Electrocardiographic waveform analysis for predicting the success of defibrillation," Crit Care Med (2000), pp. 210-211, vol. 28(11).

Povoas et al., "Predicting the success of defibrillation by electrocardiographic analysis," Resuscitation, (2002), pp. 77-82, vol. 53.

(56) References Cited

OTHER PUBLICATIONS

Robertson et al., "Defibrillator Charging During On-Going Chest Compressions: A Multi-Center Study of In-Hospital Resuscitation," American Heart Association Abstract 2644, Circulation 2009, 120(18)2:S670.

Ruiz De Gauna et al., "A method to remove CPR artifacts from human ECG using only the recorded ECG," Resuscitation, (2008), pp. 271-278, vol. 76.

Silver et al., "A New Defibrillator Mode Reduces Chest Compression Interruptions for Lay Rescuers and BLS Providers," American Heart Association Abstract P173, Circulation 2009, 120:S1479.

Sullivan et al., "How Much Can Hands-off time Be Reduced by Performing Rhythm Analysis During CPR?" American Heart Association Abstract P176, Circulation 2009, 120:S1479.

Young et al., "Amplitude spectrum area: Measuring the probability of successful defibrillation as applied to human data," Crit Care Med (2004), pp. 356-358, vol. 32(9).

Yu et al., "Adverse Outcomes of Interrupted Precordial Compression During Automated Defibrillation", Circulation, Jul. 16, 2002, pp. 368-372, vol. 106, American Heart Association, Inc.

Yu et al., "The resuscitation blanket: A useful tool for "hands-on" defibrillation," Resuscitation, (2010), pp. 230-235, vol. 81.

DEFIBRILLATOR CHARGING

CROSS-REFERENCE TO RELATED APPLICATIONS

This application is a continuation of U.S. patent application Ser. No. 15/091,694, filed Apr. 6, 2016, which is a continuation of U.S. patent application Ser. No. 13/025,327, filed on Feb. 11, 2011, which claims priority to U.S. Provisional Patent Application No. 61/304,119, filed on Feb. 12, 2010, and U.S. Provisional Patent Application No. 61/307,690, filed on Feb. 24, 2010, the entire contents of each of which are hereby incorporated by reference.

TECHNICAL FIELD

This document relates to cardiac resuscitation, and in particular to systems and techniques for assisting rescuers in performing cardio-pulmonary resuscitation (CPR).

BACKGROUND

The heart relies on an organized sequence of electrical impulses to beat effectively. Deviations from this normal sequence is known as "arrhythmia." Certain medical devices include signal processing software that analyzes electrocardiography (ECG) signals acquired from a medical patient (e.g., a victim at a scene of an emergency) to determine when a cardiac arrhythmia such as ventricular fibrillation (VF) or shockable ventricular tachycardia (VT) exists. These devices include automated external defibrillators (AEDs), ECG rhythm classifiers, and ventricular arrhythmia detectors. An AED is a defibrillator—a device that delivers controlled electrical shock to a patient—while being relatively easy to use, such as by providing verbal prompts to a provider of care to "talk" the provider through a process of evaluating a patient for, attaching the patient to, and activating, AED therapy. Certain of the medical devices just discussed are also capable of recognizing the two distinct cardiac waveforms: VT and VF.

VT is a tachydysrhythmia that originates from a ventricular ectopic focus, characterized by a rate that is typically greater than 120 beats per minute and wide QRS complexes. VT may be monomorphic (typically regular rhythm originating from a single focus with identical QRS complexes) or polymorphic (unstable, may be irregular rhythm, with varying QRS complexes). An example rhythm for an unstable VT is illustrated in FIG. 1A. Depending on the rate and the length of time that the VT has been sustained, a heart in the VT state may or may not produce a pulse (i.e., pulsatile movement of blood through the circulatory system). The cardiac activity in the VT state still has some sense of organization (note that the "loops" are all basically the same size and shape). If there is no pulse associated with this VT rhythm, then the VT is considered to be unstable and a life threatening condition. An unstable VT can be treated with an electrical shock or defibrillation.

Supraventricular tachycardia (SVT) is a rapid heartbeat that begins above the heart's lower chambers (the ventricles). SVT is an abnormally fast heart rhythm that begins in one of the upper chambers of the heart (atria), a component of the heart's electrical conduction system called the atrioventricular (AV) node, or both. Although SVT is rarely life-threatening, its symptoms, which include a feeling of a racing heart, fluttering or pounding in the chest or extra heartbeats (palpitations), or dizziness can be uncomfortable.

VF is usually an immediate life threat. VF is a pulseless arrhythmia with irregular and chaotic electrical activity and ventricular contraction in which the heart immediately loses its ability to function as a pump. VF is the primary cause of sudden cardiac death (SCD). An example rhythm for VF is illustrated in FIG. 1B. This waveform does not have a pulse associated with it. There is no organization to this rhythm (note the irregular size and shape of the loops). The pumping part of the heart is quivering like a bag of worms, and it is highly unlikely that this activity will move any blood. The corrective action for this rhythm is to defibrillate the heart using an electrical charge.

A normal heart beat wave starts at the sinoatrial node (SA node) and progresses toward the far lower corner of the left ventricle. A massive electrical shock to the heart can correct the VF and unstable VT rhythms. This massive electrical shock can force all the cardiac cells in the heart to depolarize at the same time. Subsequently, all of the cardiac cells go into a short resting period. The hope is that the sinoatrial node (SA node) will recover from this shock before any of the other cells, and that the resulting rhythm will be a pulse-producing rhythm, if not normal sinus rhythm.

Many AEDs implement algorithms to recognize the VT and VF waveforms by performing ECG analyses at specific times during a rescue event of a patient using defibrillation and cardio-pulmonary resuscitation (CPR). The first ECG analysis is usually initiated within a few seconds after the defibrillation electrodes are attached to the patient. Subsequent ECG analyses may or may not be initiated, based upon the results of the first analysis. Typically, if the first analysis detects a shockable rhythm, the rescuer is advised to deliver a defibrillation shock. Following the shock delivery, a second analysis can be initiated automatically to determine whether the defibrillation treatment was successful or not (i.e., the shockable ECG rhythm has been converted to a normal or other non-shockable rhythm). If this second analysis detects the continuing presence of a shockable arrhythmia, the AED advises the user to deliver a second defibrillation treatment. A third ECG analysis may then be executed to determine whether the second shock was or was not effective. If a shockable rhythm persists, the rescuer is then advised to deliver a third defibrillation treatment.

Following the third defibrillator shock or when any of the analyses described above detects a non-shockable rhythm, treatment protocols recommended by the American Heart Association and European Resuscitation Council require the rescuer to check the patient's pulse or to evaluate the patient for signs of circulation. If no pulse or signs of circulation are present, the rescuer can be directed to perform CPR on the victim for a period of one or more minutes. The CPR includes rescue breathing and chest compressions. Following this period of CPR, the AED reinitiates a series of up to three additional ECG analyses interspersed with appropriate defibrillation treatments as described above. The sequence of three ECG analyses/defibrillation shocks followed by 1-3 minutes of CPR, continues in a repetitive fashion for as long as the AED's power is turned on and the patient is connected to the AED device. Typically, the AED provides audio prompts to inform the rescuer when analyses are about to begin, what the analysis results were, and when to start and stop the delivery of CPR.

Many studies have reported that the discontinuation of precordial compression can significantly reduce the recovery rate of spontaneous circulation and 24-hour survival rate for victims. Thus, it is useful to recognize abnormal heart rhythms during chest compressions. There is recent clinical evidence showing that performing chest compressions before defibrillating the patient under some circumstances can be beneficial. Specifically, it is clinically beneficial to treat a patient with chest compressions before defibrillation if the response times of the medical emergency system result in a delay of more than four minutes, such that the patient is in cardiac arrest for more than four minutes. Chest compression artifact rejection can employ spectral analysis of the ECG, defibrillation success prediction, and therapeutic decision-making typically specify a set of parameters in the ECG frequency spectrum to be detected. For example, U.S. Pat. No. 5,683,424 compares a centroid or a median frequency or a peak power frequency from a calculated frequency spectrum of the ECG to thresholds to determine if a defibrillating shock is necessary.

Unfortunately, existing AEDs require batteries able to deliver large amounts of current due to the charging requirements of defibrillator high voltage capacitors. This results in batteries that are excessive in both size and weight that limit both their portability, convenience, and in the case of external, wearable defibrillators such as the LifeVest (ZOLL Medical, Chelmsford, Mass.) their wearability and comfort. In addition, batteries continue to be the least reliable element of the AEDs currently manufactured, with regular recalls resulting from manufacturing defects as well as normal end-of-life degradation that always occurs with batteries, but are particularly troublesome for life-saving equipment.

SUMMARY

The systems and techniques described here relate to control of the charging of a defibrillator, such as an AED, so as to make defibrillation readily available to an operator of the defibrillator, and also to extend battery life of the defibrillator. For example, a system may make a determination, by performing an ECG analysis while a rescuer is giving CPR, or whether a defibrillating pulse is appropriate, and may charge a capacitor or other energy providing mechanism while the user is still performing the CPR. As a result, the energy may already be stored when the time comes for the user to provide a shock.

In one implementation, a method for providing electrical therapy to a patient includes analyzing one or more electrocardiogram (ECG) signals from the patient. The method also includes selectively charging a defibrillation device based on the analysis of the one or more electrocardiogram (ECG) signals while chest compressions are being administered to the patient.

Embodiments can include one or more of the following. The method can include providing a defibrillating shock from the charged defibrillating device after chest compressions have ceased being administered. The method can include providing a defibrillating shock from the charged defibrillating device while chest compressions are being administered. The method can also include selectively charging the defibrillation device includes only charging the defibrillation device if a defibrillating shock to the victim's heart is determined, from the analysis of the ECG signals, to be suitable therapy. The method can also include, before providing the defibrillating shock, determining whether a defibrillating shock to the victim's heart is suitable therapy based on the analyzed one or more ECG signals. Selectively charging the defibrillation device can include determining, based on the analysis of the one or more ECG signals, whether to charge the defibrillation device or to instruct the user to continue chest compressions without charging the defibrillation device. Selectively charging the defibrillation device can include determining a rate of charge based on the one or more ECG signals. Selectively charging the defibrillation device can include determining a rate of charge based on a determined amount of time that remains until the end of a current chest compression cycle. Selectively charging the defibrillation device can include determining a total amount of charge based on the one or more ECG signals. Selectively charging the defibrillation device can include imposing one or more safety interlocks to prevent accidental discharge of the defibrillation device during charging of the defibrillation device. Analyzing the one or more ECG signals can include calculating an amplitude magnitude spectrum area (AMSA) value and selectively charging the defibrillation device can include selectively charging the defibrillation device or determining a rate of charge based on the calculated AMSA value. Selectively charging the defibrillation device can include charging the defibrillation device over a time period of at least about 30 seconds. Selectively charging the defibrillation device can include charging the defibrillation device over a time period of at least about 1 minute.

In some additional implementations, an external defibrillator for providing automatically controlled shock to victims of heart problems includes an electrical energy storage source and a temporary electrical storage device in electrical connection with the electrical energy storage source and capable of delivering a defibrillating shock to a human victim. The defibrillator also includes a controller programmed to analyze one or more electrocardiogram (ECG) signals and to perform charging of the temporary electrical storage device from the electrical energy storage source while directing chest compressions of the victim.

Embodiments can include one or more of the following. The external defibrillator can also include a charging device to charge the temporary electrical storage device in response to commands from the controller. The controller can be further programmed to start charging the temporary electrical storage device at a time before the end of a current chest compression cycle that is determined to substantially match a time needed to fully charge the temporary electrical storage device. The temporary electrical storage device can be a capacitor. The external defibrillator can also include electrode pads that are connected to the defibrillator, include adhesive material for adhering to the victim, and are arranged to deliver a defibrillating shock from the temporary electrical storage device to the victim. The controller can be further programmed to selectively charge the temporary electrical storage device only if a defibrillating shock to the victim's heart is determined, from the analysis of the ECG signals, to be suitable therapy. The controller can be further programmed to determine whether a defibrillating shock to the victim's heart is suitable therapy based on the analyzed one or more ECG signals. The controller can be further programmed to determine based on the analysis of the one or more ECG signals, whether to charge the temporary electrical storage device or to instruct the user to continue chest compressions without charging the temporary electrical storage device. The controller can be further programmed to determine a rate of charge for charging the temporary electrical storage device based on the one or more ECG signals. The controller can be further programmed to determine a rate of charge for charging the temporary electrical storage device based on a determined amount of time that remains until the end of a current chest compression cycle. The controller can be further programmed to determine a total amount of charge for charging the temporary electrical storage device based on the one or more ECG signals. The external defibrillator can also include one or more safety interlocks to prevent accidental discharge of the temporary electrical storage device during charging of the temporary electrical storage device. The controller can be further configured to analyze the one or more ECG signals by calculating an amplitude magnitude spectrum area (AMSA) value and selectively charge the temporary electrical storage device at a variable charging speed based on the calculated AMSA value.

Such features may provide one or more advantages in some particular implementations. For example, a defibrillator may enable a rescuer to move quickly from providing CPR to delivering a defibrillating shock, and then to continue with lifesaving efforts. Minimizing the time during which treatment has ceased may be an important factor for survival of a patient, particularly where lay responders are providing care as a bridge to the arrival of professional responders. Also, battery life for a defibrillator may be extended by charging an energy delivery device only when it is likely to be needed, and to the extent it will be needed. As a result, a defibrillator may be more likely to be usable longer, and thus available when later care may be needed. Also, the life of the defibrillator may be extended by reducing wear and tear on the device (e.g., on the capacitor) by charging an energy delivery device only when it is likely to be needed.

Other features and advantages will be apparent from the description and drawings, and from the claims.

DETAILED DESCRIPTION

This description discusses systems and techniques for providing defibrillation energy in a controlled manner. In general, such energy needs to be built up, such as by charging a capacitor, and that build up of energy may take an appreciable length of time. Using the techniques discussed here, a system can analyze a patient's needs in advance of the time to delivery defibrillation pulse (e.g., while a rescuer is performing chest compressions) and can begin charging a capacitor or other appropriate energy delivery mechanism sufficiently in advance of the time that a shock will be needed, so that the shock can be delivered as soon as it is needed.

Figure 1A:
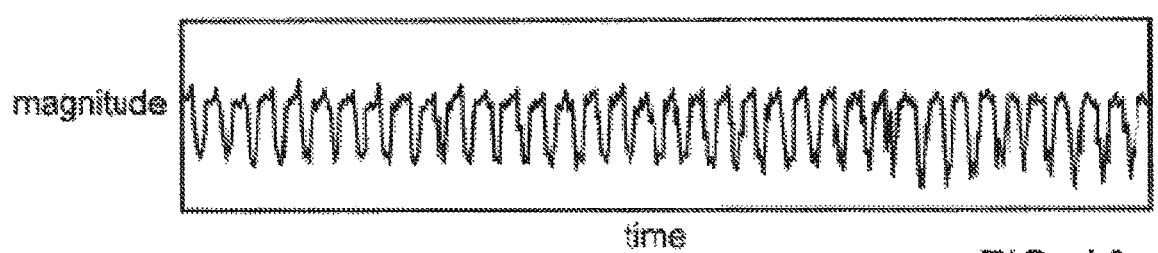
FIG. 1A is a magnitude versus time plot of a ventricular tachycardia (VT) rhythm.
Figure 1B:
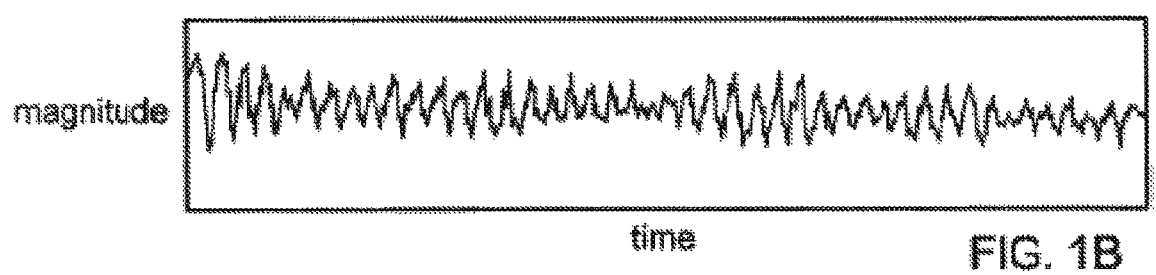
FIG. 1B is a magnitude versus time plot of a ventricular fibrillation (VF) rhythm.
Figures 2, 2A:
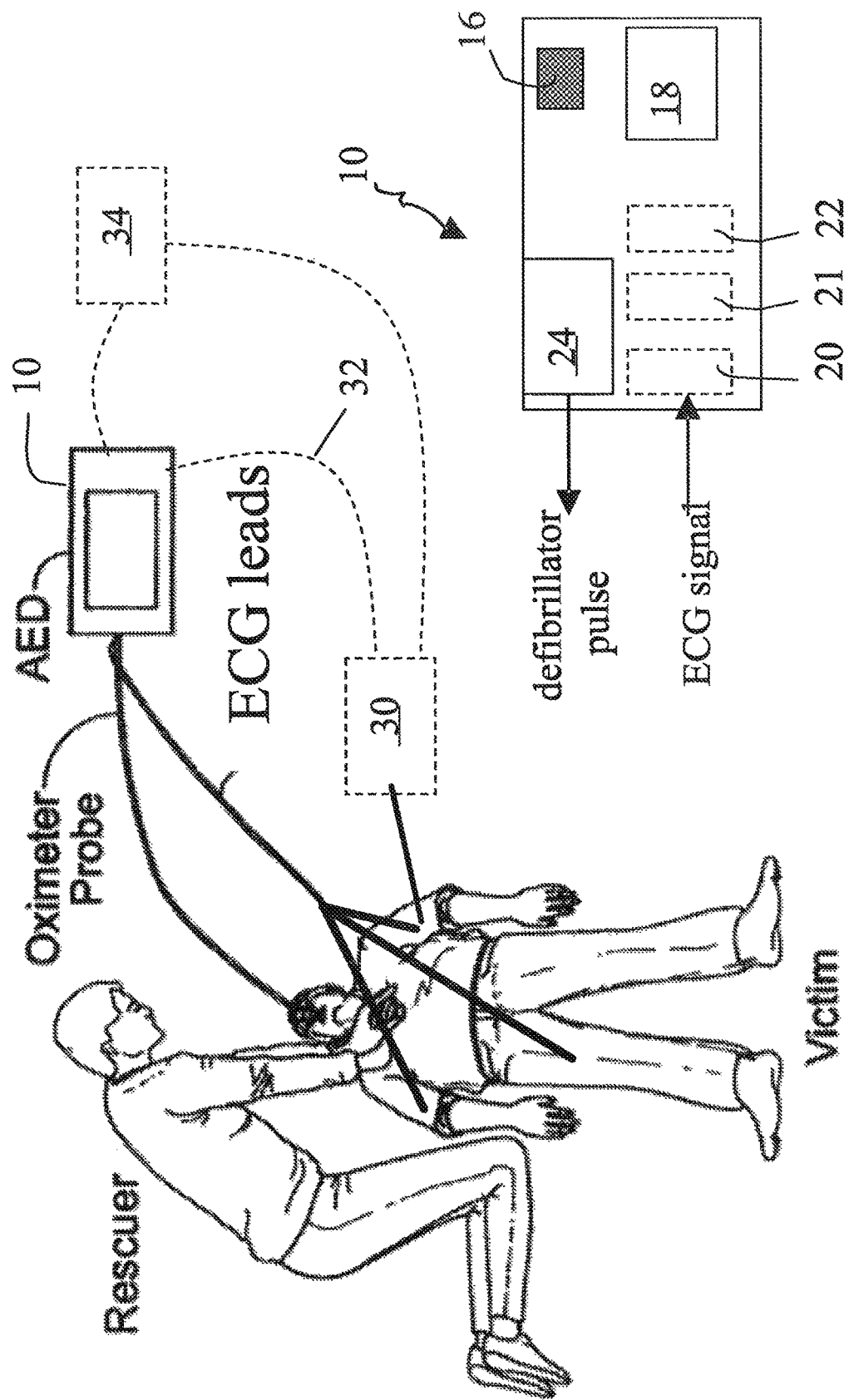
FIG. 2 is a diagram of one implementation including an automatic electronic defibrillator (AED) and a multiple lead electrocardiograph (ECG) device.
FIG. 2A is a diagram of the AED of FIG. 2.

Referring now to FIG. 2, an AED 10 is shown that may be used to provide a defibrillation shock at an appropriate time. In the figure, which shows an example implementation, a rescuer uses an AED 10 to automatically monitor a victim during cardiac resuscitation. The AED 10 uses measured ECG signals to monitor the victim's heart, and charges the defibrillation device within the AED while the victim is resuscitated using chest compressions techniques. In some examples, the manner in which the defibrillation device is charged (e.g., the rate of charge, the total amount of charge stored) can be based on the measured ECG signals. Advantageously, charging the defibrillation device during CPR chest compressions reduces the amount of time that the victim is not receiving chest compressions because, if a shockable rhythm exists, the device is armed and ready to deliver the shock as soon as the rescuer completes the chest compressions.

The AED 10 includes a speaker 16, a display screen 18, an analog-to-digital converter 20, a processor 22, and a defibrillator pulse generator 24. The analog-to-digital converter 20 is connected to a set of ECG leads that are in turn attached to the victim. The ECG leads pass signals to the processor 22 for monitoring the electrical rhythms of the victim's heart. The converter 20 sends the signals from the ECG leads to the processor 22. The processor 22 monitors the victim's heart for dangerous rhythms using the ECG signals while the victim is resuscitated using chest compressions techniques.

If the AED 10 detects a dangerous heart rhythm, the AED 10 generates an alarm signal. The alarm signal is noticeable to the rescuer. The AED 10 can generate a defibrillating shock to the victim when the rescuer issues a command to the AED 10 directing such a shock. The defibrillating shock is intended to remedy the dangerous rhythm of the victim's heart.

The AED 10 also includes a charging module 19 that is configured to charge the AED during chest compressions. The module 19 can adaptively charge the AED based on monitored ECG signals. In some examples, the defibrillator is pre-charged only if a shockable rhythm is likely to exist as determined by analysis of the monitored ECG signals. In some additional examples, the level of charge for the device is determined and set based on the monitored ECG signals. In some additional examples, the method of charging (e.g., the rate of charge) varies based on the monitored ECG signals in an effort to conserve power. For example, if time allows, a capacitor may be charged more slowly than it normally would in order to conserve power, but still ensure that the capacitor will reach its full charge just as the defibrillator is needed by the rescuer.

The AED 10 uses a rhythm advisory method for a) quantifying the frequency-domain features of the ECG signals; b) differentiating normal and abnormal ECG rhythms, such as VF; c) detecting the onset of abnormal ECG rhythms; and d) making decisions about the physiological states of the heart. This frequency-domain measure can be reliable with or without the presence of the chest compression artifact in the ECG signals. The AED 10, after identifying the current physiological state of the heart, can make a decision about appropriate therapeutic action for the rescuer to make and communicate the action to the rescuer using the speaker 16 and the display screen 18.

The AED 10 may incorporate functionality for performing additional therapeutic actions such as chest compressions, ventilations, or delivery of intravenous solution-containing metabolic or constitutive nutrients. Based on the results of the analysis of the rhythm advisory method, the AED 10 may automatically deliver the appropriate therapy to the patient.

The AED 10 may also be configured in "advisory" mode wherein the AED 10 will prompt the caregiver after the AED 10 has made a determination of the best therapy, and acknowledgement by the caregiver/device operator, in the form of a button press or voice-detected acknowledgement, is required before therapy is delivered to the patient.

The AED 10 analyzes the ECG signals to predict defibrillation success as well as to decide whether it is appropriate to defibrillate or to deliver an alternative therapy such as chest compressions, drugs such as epinephrine, constitutive nutrients such as glucose, or other electrical therapy such as pacing.

In some examples, one or more therapeutic delivery devices 30 automatically deliver the appropriate therapy to the patient. The therapeutic delivery devices 30 can be, for example, a portable chest compression device, a drug infusion device, a ventilator and/or a device that includes multiple therapies such as defibrillation, chest compression, ventilation and drug infusion. The therapeutic delivery devices 30 are physically separate from the defibrillator AED 10, and control of the therapeutic delivery devices 30 may be accomplished by a communications link 32. The communications link 32 may take the form of a cable but preferably the link 32 is via a wireless protocol.

In other examples, control and coordination for the overall resuscitation event and the delivery of the various therapies may be accomplished by a device 34 or processing element that is external to the AED 10. For instance, the device 34 may download and process the ECG data from the AED 10; analyze the ECG signals, perform relevant determinations like those discussed above and below based on the analysis, and control the other therapeutic devices 30, including the AED 10. In other examples, the AED 10 may perform all the processing of the ECG, including analyzing the ECG signals, and may transmit to the control device 34 only the final determination of the appropriate therapy, whereupon the control device 34 would perform the control actions on the other linked devices 30.

Chest compression artifacts can be separated from the ECG signal components, making it possible for the AED 10 to process the ECG signal without halting the processing during chest compressions. Exemplary methods for analyzing the ECG signal to determine if a shockable rhythm exists are described, for example, in U.S. Pat. No. 7,565,194, titled "ECG Rhythm Advisory Method," the contents of which are hereby incorporated by reference in their entirety.

It has been recognized that good chest compressions during CPR is essential to saving more victims of cardiac arrest. The compression rate recommended by the American Heart Association in its guidelines is greater than 100 compressions per minute. Many studies have reported that the discontinuation of chest compressions, such as is commonly done for ECG analysis and charging of a defibrillator, can significantly reduce the recovery rate of spontaneous circulation and 24-hour survival rate. Because of safety issues with delivery of a high voltage defibrillation shocks with voltages of 1000-2000 volts, rescuers are taught to cease chest compressions and remove their hands from the victim's chest before initiating the defibrillation shock. By analyzing ECG signals during chest compressions as a mechanisms to permit earlier charging of an energy delivery device (e.g., a capacitor) in a defibrillator device, the gaps in providing chest compressions can be reduced, and patient care increased.

Figure 3A:
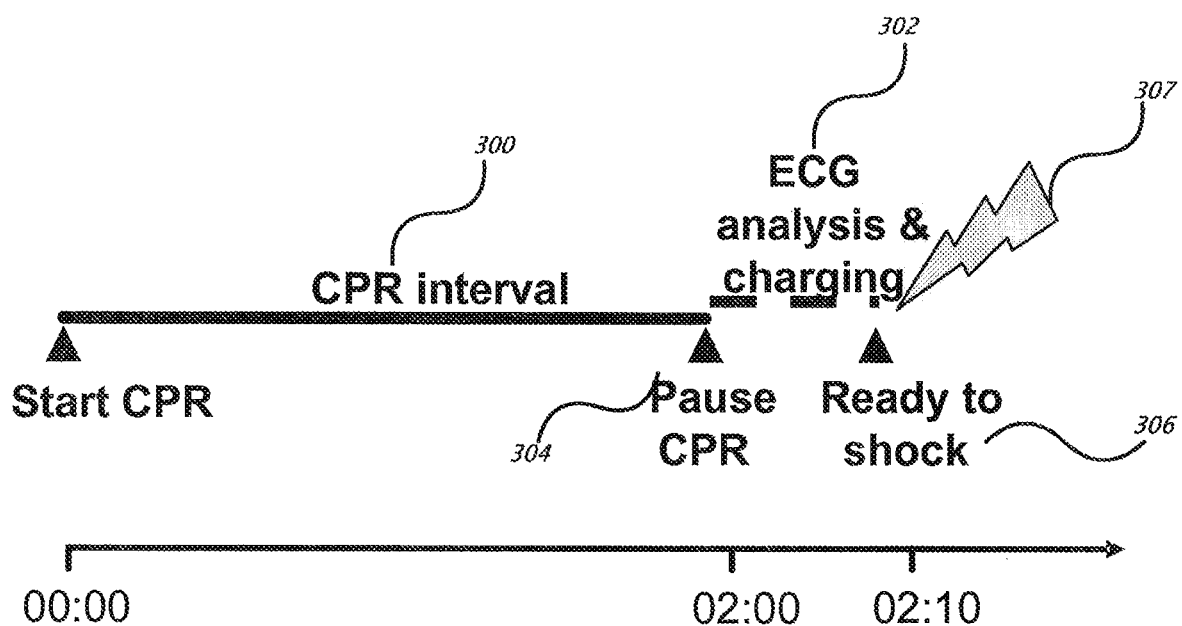
FIGS. 3A and 3B are examples of ECG analysis and charging cycles.

FIG. 3A shows an example of an ECG analysis and charging cycle in which charging of a defibrillator device starts after a CPR interval has ended. As shown in the figure, in operation of some AED devices, the rescuer is instructed to perform chest compressions for a two minute CPR interval 300 after which the rescuer is instructed to pause his or her performance of CPR 304. At this point, the rescuer removes his or her hands from the victim, ECG analysis is performed, and the defibrillator device is charged (interval 302). As such, a time period elapses (time period 302) during which the rescuer is not delivering chest compressions to the victim. This elapsed time period before delivery of the shock 307 can be, for example, about 10 seconds—of which a portion is devoted to performing the ECG analysis and a portion is devoted to charging the defibrillation device. While methods exist for processing ECG signals without halting the processing during CPR chest compressions, a time period may still elapse between the cessation of chest compressions and availability of an adequate charge for delivering a shock.

Figure 3B:
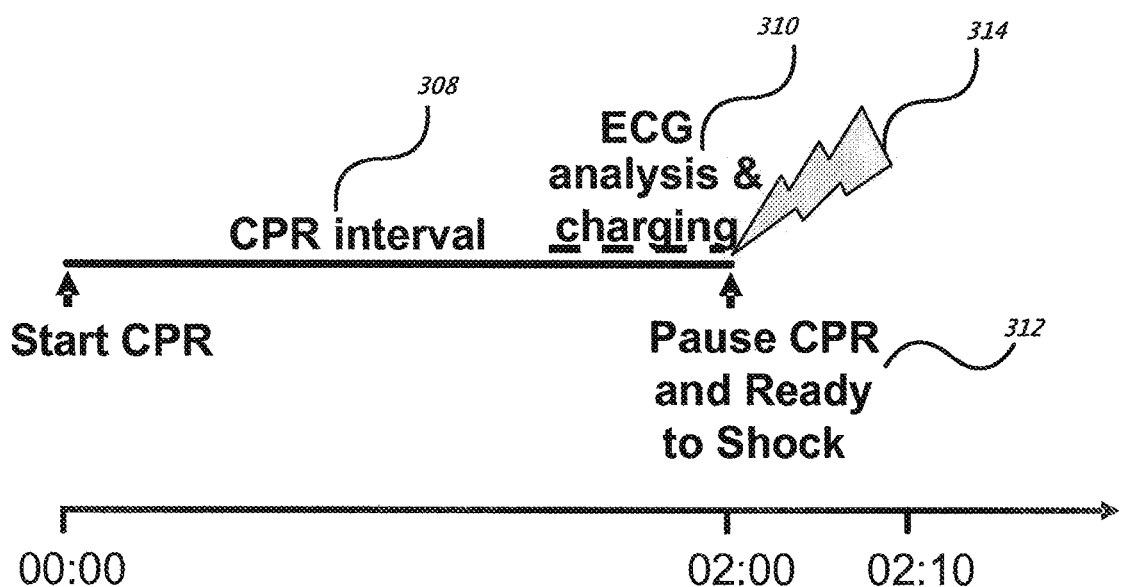

FIG. 3B shows an example of an ECG analysis and charging cycle in which charging of a defibrillator device starts before a CPR interval has ended. The CPR interval can be based on a length of time of administration of chest compressions (e.g., as shown in FIG. 3B), a total number of chest compressions, a total number of effective chest compressions based on depth or rate of the compression, a total length of time of effective chest compressions, or can be variable based on one or more observed factors such as the ECG analysis. The CPR interval can additionally be updated by software or firmware to handle different CPR protocols such that the device is charged and the defibrillation therapy is delivered according to the protocol. As shown in the figure, in operation methods described herein, the defibrillation device is charged while the rescuer is providing the CPR chest compressions. Similar to the method described with respect to FIG. 3A, the rescuer is instructed to perform chest compressions for a two minute CPR interval 308. During the two minute CPR interval, ECG analysis is performed and the defibrillator device is charged (interval 310). After the CPR interval is complete, the rescuer is instructed to pause CPR 312, and shock 314 can be delivered almost immediately to the victim because the defibrillator device has already had time to charge. Because the defibrillator device is fully charged before the rescuer ceases chest compressions, the time period during which the rescuer is not delivering chest compressions to the victim can be greatly reduced and the shock can be delivered immediately or almost immediately after chest compressions are completed. For example, the elapsed time between the end of the CPR interval and the delivery of the shock (if a shockable rhythm exists) can be less than about 5 seconds (e.g., less than about 5 seconds, less than about 3 seconds, less than about 2 seconds, less than about 1 second, less than about ½ a second). In some embodiments, the length of time between the rescuer ceasing chest compressions and delivery of the shock can be simply based on the amount of time the rescuer spends locating and pressing a button on the AED device that causes the AED device to deliver the shock to the victim.

In some additional embodiments, the AED device may utilize a brief period of time (e.g., while the rescuer locates and presses the button) after the rescuer ceases chest compressions to reconfirm the desirability of delivering the shock to the victim. For example, a rescuer can be instructed to visually inspect and confirm that a shockable rhythm exists and/or the AED device can continue to collect and analyze ECG signals (in the absence of chest compressions resulting in less artifacts in the ECG signal) to re-confirm the desirability of delivering the shock. In general, a time period for re-confirmation based on analysis of an ECG signal without chest compression artifacts can be brief (e.g., less than about 5 seconds, less than about 3 seconds, less than about 2 seconds). The time period for re-confirmation can be based on physiological characteristics (e.g., heart rate that is fast or slow) and/or a desired confidence level for the ECG analysis.

Because of safety issues with charging the defibrillation device to a voltage of 1000-2000 volts while the rescuer is in contact with the victim, safety interlocks can be included in a defibrillator device to ensure that the voltage is not discharged before the rescuer removes his or her hands from the victim. The defibrillator safety interlocks can include one or more software-controlled-hardware and/or software mechanisms that prevent the defibrillator from accidentally discharging outside of the unit. In order for the defibrillator to deliver a shock, the AED device confirms that a variety of software and hardware states are met during the charging process. Once the defibrillator reaches a full level of charge, a therapy button is enabled. Enabling the therapy button removes a final hardware safety interlock and selects the output for the therapy charge to the patient connector instead of the internal resistor network used to dissipate charge when a shock is not delivered. Once enabled, a rescuer presses the therapy button and the AED registers the press which closes a therapy delivery relay and delivers the defibrillation pulse. The safety interlocks control the enablement of the therapy button and a do not allow the rescuer to deliver a shock to the victim until other actions occur that disable the safety interlocks.

In some additional methods, an electrically insulating protection layer extends over the surface of the patient so that manual compressions may continue safely and unabated during the charging of the defibrillation device and delivery of the defibrillation shock. An exemplary electrically insulating protection layer is described, for example, in U.S. Pat. No. 6,360,125, which is incorporated by reference herein in its entirety.

In some embodiments, the period for administration of chest compressions is not preset, rather the period can be variable based on the observed EGC signals. ECG analysis may start while CPR chest compressions are being administered. When the AED device determines that a shockable rhythm exists based on the ECG signals or otherwise makes a determination that the appropriate therapy would be to deliver the defibrillation shock, the AED device can begin charging. CPR chest compressions continue while the device is charging. The AED device can optionally instruct the rescuer of an amount of time that he/she should continue to administer chest compressions based on the length of time used to charge the defibrillator device. Once the device is fully charged, the rescuer can be the victim.

Figure 4A:
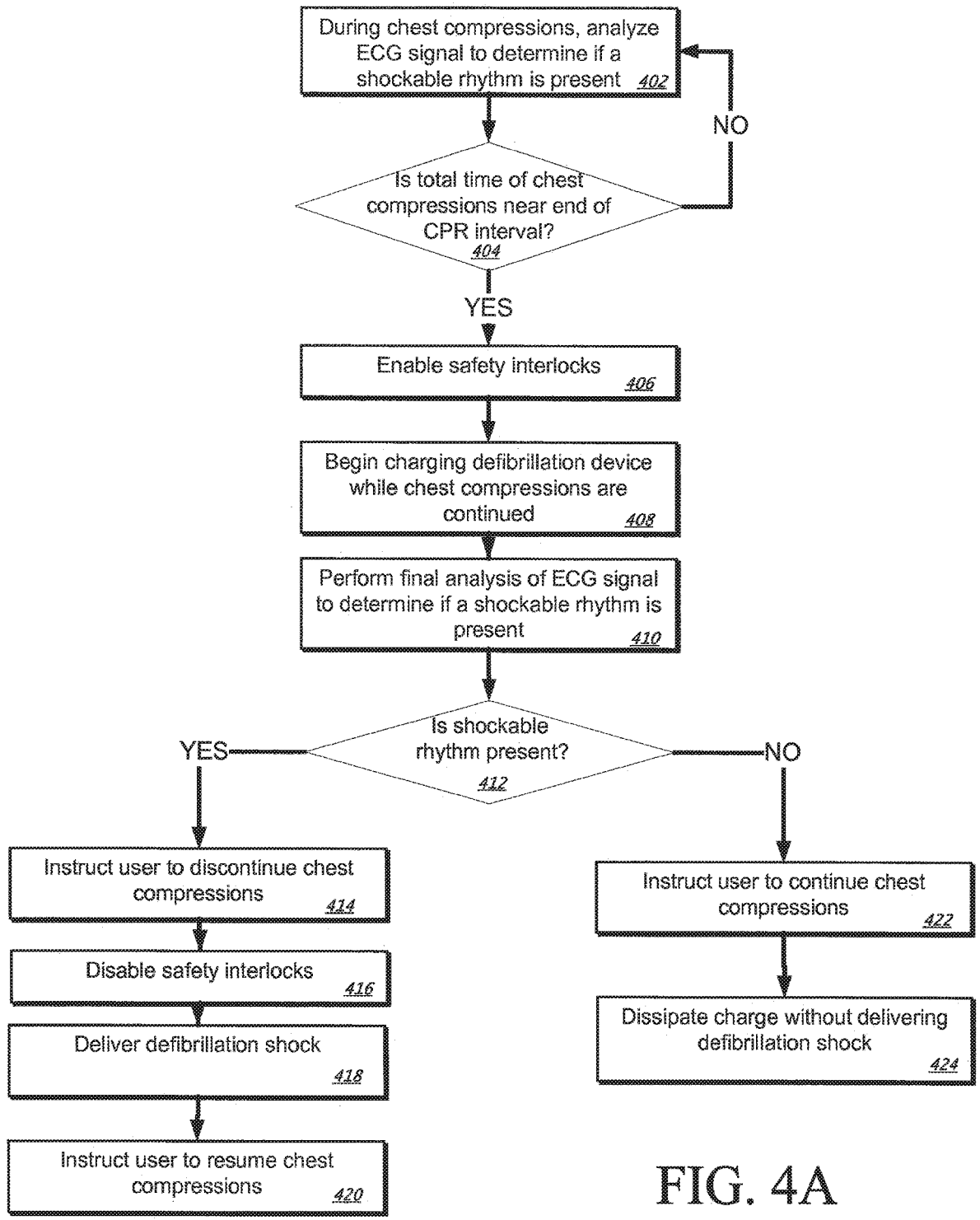
FIG. 4A is a flow chart showing actions taken to charge a defibrillation device during chest compressions associated with a CPR interval.

FIG. 4A is a flow chart showing actions taken to charge a defibrillation device during chest compressions associated with a CPR interval. As noted above, charging the defibrillation device in addition to analyzing an ECG signal during chest compressions can provide the advantage of reducing the amount of time that a rescuer is not administering chest compressions to the victim. In general, an interval (e.g., a set length of time) is set for the administration of chest compressions. During this interval, the system analyzes an ECG signal and charges the defibrillation device. Safety interlocks are enabled that prevent accidental dissipation of the charge in the defibrillation device during the CPR chest compression interval. At the end of the CPR interval, a decision of whether to shock the victim is made based on the ECG signal analysis, and the stored charge is either administered to the victim or dissipated internally.

The example process here begins at box 402, where the AED analyzes an ECG signal to determine if a shockable rhythm is present in the victim. The ECG signal is measured while chest compressions are being administered to the victim. As such, the AED separates the chest compression artifact from the ECG signal components to process the ECG signal without halting the processing during CPR chest compressions (e.g., as described in U.S. Pat. No. 7,565,194).

At box 404, the AED determines if the current time is near the end of the CPR interval (e.g., within about 10-30 seconds of the end of the CPR interval). Exemplary CPR intervals can be between 2 and 5 minutes (e.g., 2 minutes, 3 minutes, 4 minutes, and 5 minutes). If the current time within a determined window for performing chest compressions is not near the end of the CPR interval, the AED device continues to analyze the ECG signals (box 402). If the current time is near the end of the CPR interval, the AED enables safety interlocks at box 406 (though the interlocks may be enabled even before this time).

As the chest compressions continue, the AED begins charging the defibrillation device at box 408 with the safety interlocks enabled. The amount of time needed to charge the defibrillation device can vary based on the current used to charge the device and the total amount of charge desired. As such, the system begins charging the defibrillation device in advance of the end of the CPR interval such that the defibrillation device will be fully charged at the end of the CPR interval. For example, a window for performing CPR can be determined when the CPR cycle begins, a time for charging the defibrillation device can be looked up or otherwise determined, and the system may be programmed to check, at a time in advance of the end of the window that substantially corresponds to the charging time, for whether a shockable rhythm is present At box 410, the AED performs a final analysis of the ECG signal to determine if a shockable rhythm is present in the victim. Exemplary methods for analyzing the ECG signal to determine if a shockable rhythm exists are described, for example, in U.S. Pat. No. 7,565,194, titled "ECG Rhythm Advisory Method," the contents of which are hereby incorporated by reference in their entirety. If a shockable rhythm is not observed, at box 422, the AED instructs the rescuer to continue chest compressions. Thus, if a shockable rhythm does not exist, the victim receives uninterrupted chest compressions. Such chest compressions may not place the heart back into normal operation, but they may nonetheless maximize perfusion of blood through the heart until a more highly-trained rescuer can arrive and take over.

At box 424, the AED dissipates the charge from the defibrillation device without delivering a shock to the victim. For example, the AED can dissipate the stored charge using a resistor network inside the AED device such that the charge can be dissipated without requiring the rescuer to discontinue chest compressions. The dissipation may occur by dumping the charge, for example. The charge may also be "recycled" back into a battery on the device so as to extend the battery life.

If a shockable rhythm is observed, at box 414, the AED device instructs the rescuer to discontinue chest compressions. For example, the AED device can provide audible instructions to the rescuer via a speaker and/or can provide a visual instruction to the rescuer via a display device. At box 416, the AED disables the safety interlocks, thus making it possible for the shock to be delivered through electrodes that are attached to the victim.

At box 418, the AED device delivers the defibrillation shock to the victim. Such delivery may occur in response to the rescuer pressing a button on the AED to provide a command to delivered the shock. The shock may also be delivered automatically, such as after the AED voices a command to stand clear of the victim. The shock is delivered without significant delay after the cessation of chest compressions because the device has been previously pre-charged while the chest compressions were being administered.

At box 420, the AED device instructs the user to resume chest compressions. This initiates another CPR cycle during which a similar ECG analysis will be performed. The process just described may thus be repeated until a shock succeeds in placing the victim's heart roughly back into a normal operating mode, or until additional caregivers arrive to attempt different resuscitation approaches.

In some embodiments, a reconfirmation of the desirability to deliver the defibrillation shock to the victim is performed after the rescuer ceases chest compressions. Because the re-confirmation is performed when the rescuer is not delivering chest compressions, the ECG signals analyzed by the AED device during the reconfirmation are expected to be less noisy and have less artifacts because artifacts from the chest compressions are no longer present. As such, an ECG analysis may have higher degree of confidence. In general, as described above, a time period for re-confirmation based on analysis of an ECG signal without chest compression artifacts can be brief (e.g., less than about 5 seconds, less than about 3 seconds, less than about 2 seconds).

In some embodiments, the AED device can determine whether to perform a reconfirmation analysis based on one or more factors associated with the prior EGC analysis such as a certainty value. For example, if the prior EGC analysis results in a high certainty that delivering the defibrillation shock to the victim is the appropriate therapy (e.g., a high certainty of conversion to a perfusing rhythm) then the AED may deliver the shock nearly immediately after the rescuer ceases chest compressions (e.g. without a reconfirmation period). On the other hand, if the prior EGC analysis has a lower certainty that delivering the defibrillation shock to the victim is the appropriate therapy then the AED may perform a reconfirmation analysis before making a final determination of whether to deliver the defibrillation shock. Additionally or alternatively a determination of whether to perform a reconfirmation analysis can be based on a confidence value associated with the level of confidence that the EGC signal analysis is correct. For example, if the signal is extremely noisy and has a large presence of artifacts, the confidence of the analysis may be lower making it desirable to reconfirm the analysis in the absence of the chest compressions.

Figure 4B:
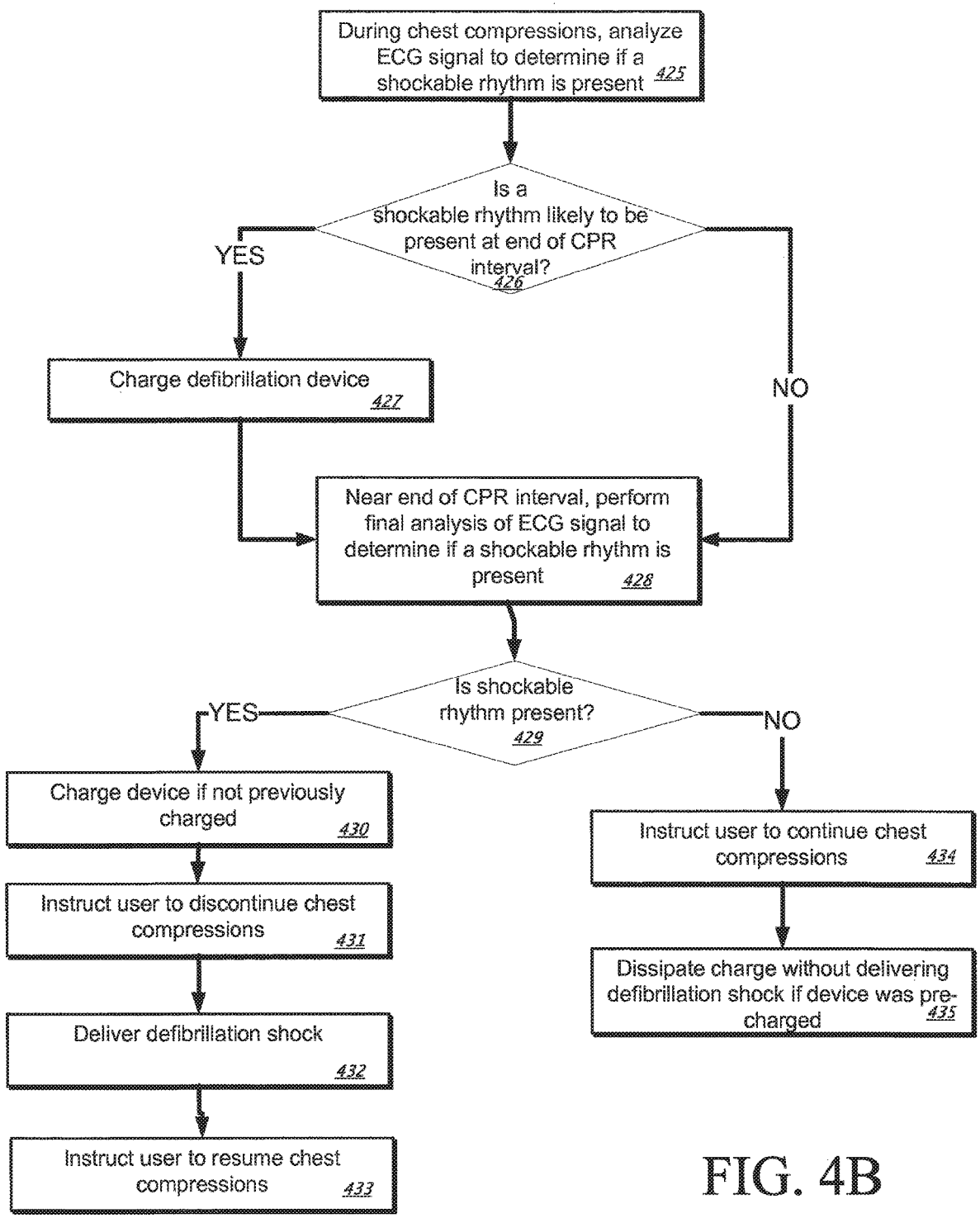
FIG. 4B is a flow chart showing actions taken to charge a defibrillation device using different current levels that are selected based on the likelihood of a shockable rhythm being observed.

FIG. 4B is a flow chart showing actions taken to charge a defibrillation device using different current levels that are selected based on the likelihood of a shockable rhythm being observed. Portable AED devices may be powered by a battery or other power supply having a limited lifetime. In order to conserve power for future uses of the AED device or for the administration of multiple shocks to a single victim, various charging algorithms can be used. In some examples, an AED device makes a determination of whether a shockable rhythm exists in the victim and only charges the defibrillator device if a shockable rhythm exists. Such a charging algorithm conserves power because if a shockable rhythm is not observed, the AED device does not charge the defibrillator and then dump or dissipate the charge.

The example process begins at box 425, where the AED analyzes an ECG signal while chest compressions are being administered to a victim to determine if a shockable rhythm is likely to be present in the victim at the end of the CPR interval (e.g., as described in U.S. Pat. No. 7,565,194). At box 426, the AED determines if a shockable rhythm is likely to be present in the victim at the end of the CPR interval. While the CPR interval will continue regardless of the outcome of the analysis, the determination is used to decide whether to begin charging the defibrillator device. The time at which to make such a determination may be set by a determination of how long it will take to charge the defibrillator device. When different possible rates of charge are available to the system, and maximum time charge can be set for the ECG analysis, a rate of charge may be determined, and then the actual charging may begin at a time preceding the end of CPR that is substantially the amount of time the charge will take at the computed rate of charge.

A threshold for determining whether to pre-charge the defibrillator can be different from a threshold used to determine whether to administer a shock to the victim. For example, because the determination is used to decide whether to pre-charge the AED device, a lower threshold may be used such that the device will be fully charged at the end of the CPR interval if a shock may be administered. For example, an accuracy measure can be used to set the thresholds. For example, an observed signal resulting in a high accuracy value (e.g., a confidence of greater than about 90%) can be used as to set a threshold for determining whether to administer a defibrillation shock to the victim while a lower confidence (e.g., a confidence of 50% or greater) can be used to set a threshold for determining whether to begin charging the defibrillation device. For example, an AMSA number that is associated with a certain accuracy level in predicting a successful conversion can be used to set the thresholds for deciding whether to pre-charge the defibrillator, the rate of charging the defibrillator, and whether to administer the defibrillation shock. This AMSA number can be customized based on a request of the rescuer or the medical director. For example, an AMSA number that is associated with a accuracy level of 90% or greater (e.g., 90% or 95%) in predicting a successful conversion can be used to set the threshold for administering a defibrillation shock and an AMSA number that is associated with a accuracy level of 70% or greater (e.g., 70%, 80%, 90%) in predicting a successful conversion can be used to set the threshold for deciding whether to pre-charge the defibrillator. In other examples, an AMSA number that is associated with an accuracy level of 70% or greater (e.g., 70%, 80%, 90%) in predicting a successful conversion can be associated with the fastest possible rate in charging the defibrillator; The lower value the AMSA number is, the rate of charging is set to (e.g., half speed in charging when an AMSA number associated with an accuracy level of 50% is observed). In some embodiments, other predictors of conversion success (e.g., SCE) can be used.

If a shockable rhythm is not likely to be present in the victim at the end of the CPR interval, the AED continues to receive and analyze the ECG signals. At box 428 near the end of the CPR cycle, the AED device performs a final analysis of the ECG signal to determine whether a shockable rhythm exists. This second determination of whether a shockable rhythm exists serves as a confirmation that a shockable rhythm still does not exist, so that a rescuer does not forego providing a shock to the victim in a situation where the patient's condition has changed in a manner that would make a shock would be beneficial.

In contrast, if the system determines that a shockable rhythm is likely to exist, at box 427, the AED pre-charges the defibrillation device. This charging occurs while the rescuer is administering the CPR chest compressions. At box 428 near the end of the CPR cycle, the AED device performs a final analysis of the ECG signal.

At box 429, the AED device determines whether a shockable rhythm exists. This second determination of whether a shockable rhythm exists serves as a confirmation that a shockable rhythm still exists, so that a rescuer is not led to give a shock to a patient when the patient's condition has changed in a manner that would make the shock essentially futile. A different threshold can be used for the determination of whether to administer the shock to the victim than was used to determine whether to pre-charge the defibrillator.

If a shockable rhythm does not exist at this later time and under this later standard (though the standard may also be the same for deciding whether to pre-charge and deciding whether to remove the safety interlocks and allow the shock actually to be delivered), the AED instructs the rescuer to continue chest compressions at box 434 such that the victim receives uninterrupted chest compressions. At box 435, the AED dissipates the charge (e.g., using one or more of the methods described herein) from the defibrillation device without delivering a shock to the victim if the device was pre-charged (e.g., at box 427).

If a shockable rhythm is observed, at box 430, the AED device determines whether the defibrillator was pre-charged (e.g., at box 427) and charges the defibrillator if it was not previously pre-charged (or completes any still-incomplete charging). At box 431, the AED device instructs the rescuer to discontinue chest compressions (e.g., using one or more of the methods described herein). At box 432, the AED device delivers the shock and at box 432, the AED device instructs the user to resume chest compressions. This initiates another CPR cycle during which a similar ECG analysis will be performed.

Figure 4C:
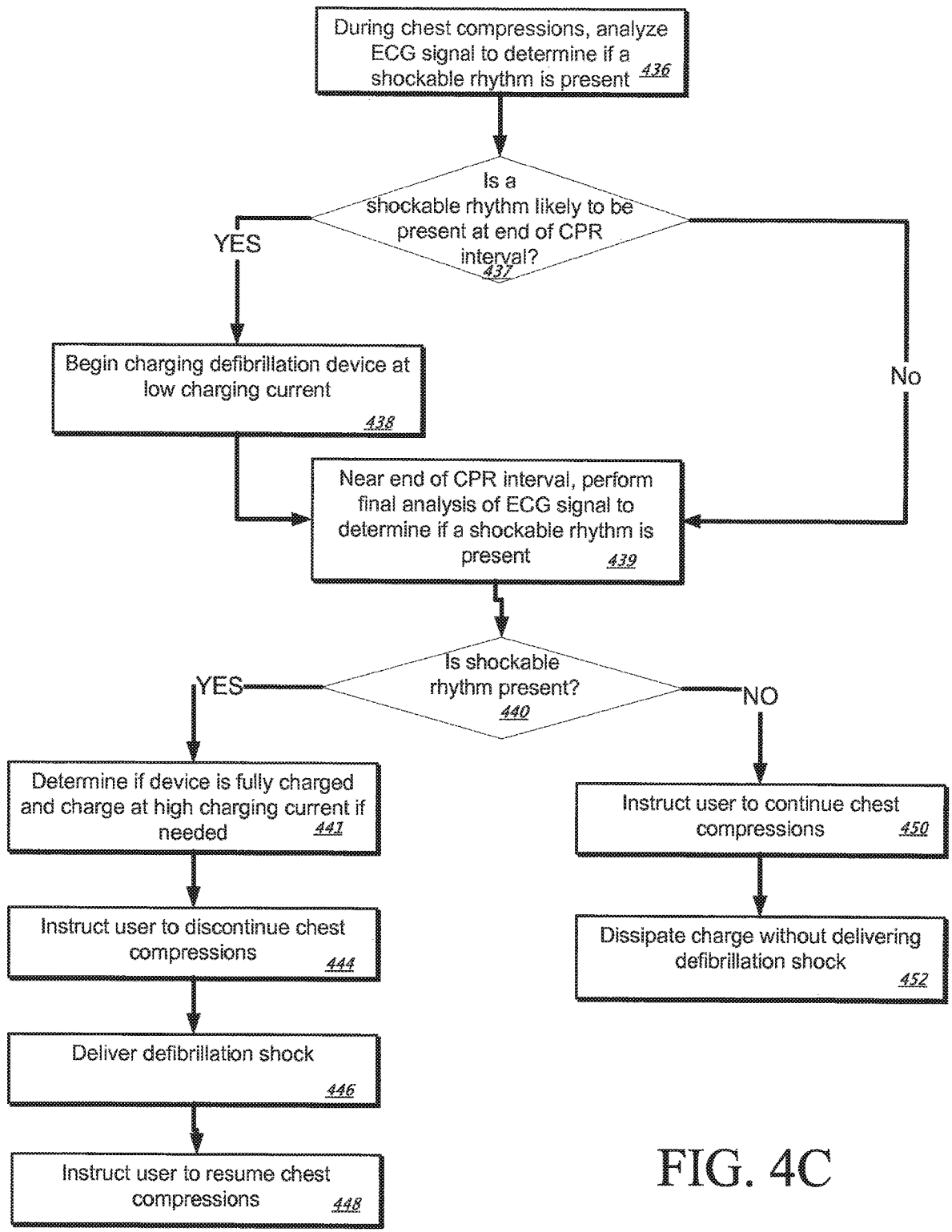
FIG. 4C is a flow chart showing actions taken to adaptively charge a defibrillation device using different current levels based on the likelihood of a shockable rhythm being observed.

FIG. 4C is a flow chart showing actions taken to charge a defibrillation device using different current levels based on the likelihood of a shockable rhythm being observed. One exemplary way to conserve power in an AED is to charge the AED device at a lower current over a longer period of time (e.g., over a period of at least 30 seconds), resulting in less of a drain on the batter power as compared to charging the AED device to the same total charge using a higher current and a shorter period of time (e.g., over a period of at most 10 seconds). A percentage calculated by dividing the lower charging current by the higher charging current can be greater than about 50% (e.g., greater than about 50%, greater than about 60%, greater than about 75%) and less than about 90% (e.g., less than about 90%, less than about 80%).

Charging the AED device over a longer period of time at a lower current can occur during the CPR interval because the typical CPR interval is between 2-5 minutes. Both charging the device at a lower current (that is selected to permit full or substantially full charging during the available charging interval before a shock may be needed) and/or only charging the device if it is likely that a shock will be administered to the victim can contribute to an extended battery life for the AED device. Drawing less total current from the battery can provide additional advantages such as enabling the use of a smaller battery (and thereby enabling a smaller and lighter AED) and/or enabling the use of alternative power devices such as solar power and/or human generated power.

In one embodiment, a "crank" generator may be employed. Since the time available to charge the defibrillator capacitor can be increased to as much as 3-10 minutes using the systems described herein, a 200 joule capacitor only requires at most approximately a 1.5 watt power source, assuming a 3 minute charge duration and a high voltage flyback circuitry efficiency of 75%. Due to leakage of a typical film capacitor at maximum voltage of approximately 2 Watts, a generator of 2.5-3 Watts would be required. Such a power supply may be an external hand crank power supply available commercially (SuperBattery with Crank Generator, Teledex, Inc., N.J.), or a built-in crank generator in the defibrillator with a power output sufficient to charge the defibrillator capacitor in the allotted time. As part of the generator, an additional energy storage element will preferably be included, for instance a battery as contained in the Superbattery described above, or a so-called "ultracapacitor", such as that manufactured by Maxwell Technologies (San Diego), for instance the 350 Farad, part number BCAP0350 E270 T11. The ultracapacitor is used to maintain power for the low-voltage circuitry such as signal amplifiers and digital processing circuitry when the rescuer has stopped providing mechanical energy to the generator. The mechanical energy for the generator may alternatively be contained in a structure positioned on the patient's sternum, which will be compressed during cardiopulmonary resuscitation. Currently, devices exist commercially (CPR-STATPADZ, ZOLL Medical, Chelmsford, Mass.) which measure the performance of the rescuer doing chest compressions by measuring the compression depth via an accelerometer sensor within a low-profile housing positioned under the rescuers hands while they are compressing the patient's sternum during CPR. The housing may additionally be constructed to flexibly deform during sternal compressions, thus causing motion of the actuator of a generator, for instance a linear motion electric power generator as described in U.S. Pat. No. 5,818,132. A typical patient requires approximately 100 pounds of force to depress the sternum to the required depth of 2 inches, as per the American Heart Association recommendations. Thus, by allowing for a deformation of the housing of 0.5-1 inches would increase the compression depth of the rescuer to 2.5-3 inches to achieve the same sternal depth of 2 inches, but would provide the requisite 2.5-3 Watts of necessary power, assuming a generator efficiency of 40%. Alternatively, the housing may be a spring-loaded two piece housing with accelerometer and generator contained within the housing, the upper portion of the generator actuator affixed to the upper portion of the housing, the generator and the lower portion of the actuator affixed to the lower housing, and power generated when the spacing between the upper and lower housings is changed.

In another embodiment, the lid of the AED might be surfaced with a solar cell, thus providing approximately 100 square inches of available surface area. Standard, commercially available amorphous Silicon crystal cells currently provide approximately 45 milliwatts per inch squared. This power can be doubled by employing a more expensive crystalline cell as well as alternative structures. Thus, the solar cell would be able to provide 4-10 Watts of power, which is more than sufficient for the systems described herein. As with the human powered generator approach, an electrical energy storage element would be included, such as an ultracapacitor, in addition to the defibrillator capacitor, for powering the analog and digital low-voltage electronics, if for instance a shadow from the rescuer passes in front of the solar cells during device use. Thus, even with batteries that have failed or whose performance has degraded to the point that they are unable to power the defibrillator, it is now possible to have a backup power source for use in emergencies, not currently available with existing technology. In the preferred embodiment, a fail-safe switch, relay or transistor would be employed that would disconnect the failed batteries from the electronics, so that power would not be diverted from the generator or solar cell by the batteries during operation.

Because the defibrillator capacitor can be charged over a significantly increased period of time, the peak charging current is significantly decreased by a factor of ten or more. This allows for significantly smaller batteries to be used to power the defibrillator. In general, the batteries can include one or more primary cells and/or one or more secondary (e.g., rechargeable) cells. Examples of significantly smaller batteries that can be used to power the defibrillator include any battery (or combination of multiple batteries) with a relatively low power output of, for example, less than about 10 W (e.g., less than about 10 W, less than about 7 W, less than about 5 W, less than about 4 W, less than about 3 W). In some examples, the power output can be greater than about 2.5 W and less than 10 W (e.g., between about 2.5 W and about 10 W, between about 2.5 W and about 7 W, between about 2.5 W and about 5 W, between about 2.5 W and about 4 W, between about 2.5 W and about 3 W). In one particular example, the current ZOLL AEDPlus uses ten lithium CR123 commercial batteries to power the defibrillator, at a significant size, weight and cost expense. With the systems and charging methods described herein, this can be reduced to 1, or at most, 2 CR123 batteries. In addition, it is now possible to use even smaller alkaline batteries, such as a standard commercially-available 'C' size alkaline cell.

At box 436, while chest compressions are being administered, the AED analyzes an ECG signal (e.g., as described in U.S. Pat. No. 7,565,194) and at box 437, the AED determines if a shockable rhythm is likely to be present in the victim at the end of the CPR interval. While the CPR interval will continue regardless of the outcome of the analysis, the determination is used to decide whether to begin charging the defibrillator device.

If a shockable rhythm is not likely to be present in the victim at the end of the CPR interval, the AED continues to receive and analyze the ECG signals. At box 439, near the end of the CPR cycle, the AED performs a final analysis of the ECG signal to determine whether a shockable rhythm exists. The analysis may also continue until a shockable rhythm is present.

In contrast, if the system determines that a shockable rhythm is likely to exist (either initially or upon further monitoring and analysis), at box 438, the AED device begins pre-charging the defibrillation device at a low charging current. In other examples, the charging current can be based on the length of time remaining in the CPR interval. For example, a charging current can be selected such that the device will be fully charged at the end of the CPR interval. This may result in the charging occurring at a low rate over an extended period of time (e.g., over a period of time greater than about 30 seconds, over a period of time greater than about 45 seconds, over a period of time greater than about 1 minute). For example, if a shockable rhythm is determined initially, the charging rate may be relatively low, whereas if there was no initial shockable rhythm but the device senses a shockable rhythm later in the chest compression cycle, the charging rate may be relatively fast. This charging occurs while the rescuer is administering the CPR chest compressions (though some may occur after the end of the provision of CPR chest compressions, though not enough that it would create an substantial effect on the timing of the CPR).

At box 439 near the end of the CPR cycle, the AED device performs a final analysis of the ECG signal, and at box 440, the AED device determines whether a shockable rhythm exists. If a shockable rhythm does not exist, the AED instructs the rescuer to continue chest compressions at box 450 such that the victim receives uninterrupted chest compressions. At box 452, the AED dissipates the charge (e.g., using one or more of the methods described herein) from the defibrillation device without delivering a shock to the victim if the device was pre-charged (e.g., at box 438).

If a shockable rhythm is observed, at box 441, the AED device determines whether the defibrillator has reached a full level of charge and charges the defibrillator to the full level of charge (if needed) at a high current. For example, while the pre-charging can occur at a low current over an extended period of time, charging to reach the full charge if the device is not fully charged in time (or charging if not pre-charged) can occur at a high current and during as short of period as is practical.

At box 444, the AED device instructs the rescuer to discontinue chest compressions (e.g., using one or more of the methods described herein). At box 446, the AED device delivers the shock and at box 448, the AED device instructs the user to resume chest compressions. This initiates another CPR cycle during which a similar ECG analysis will be performed.

Figure 4D:
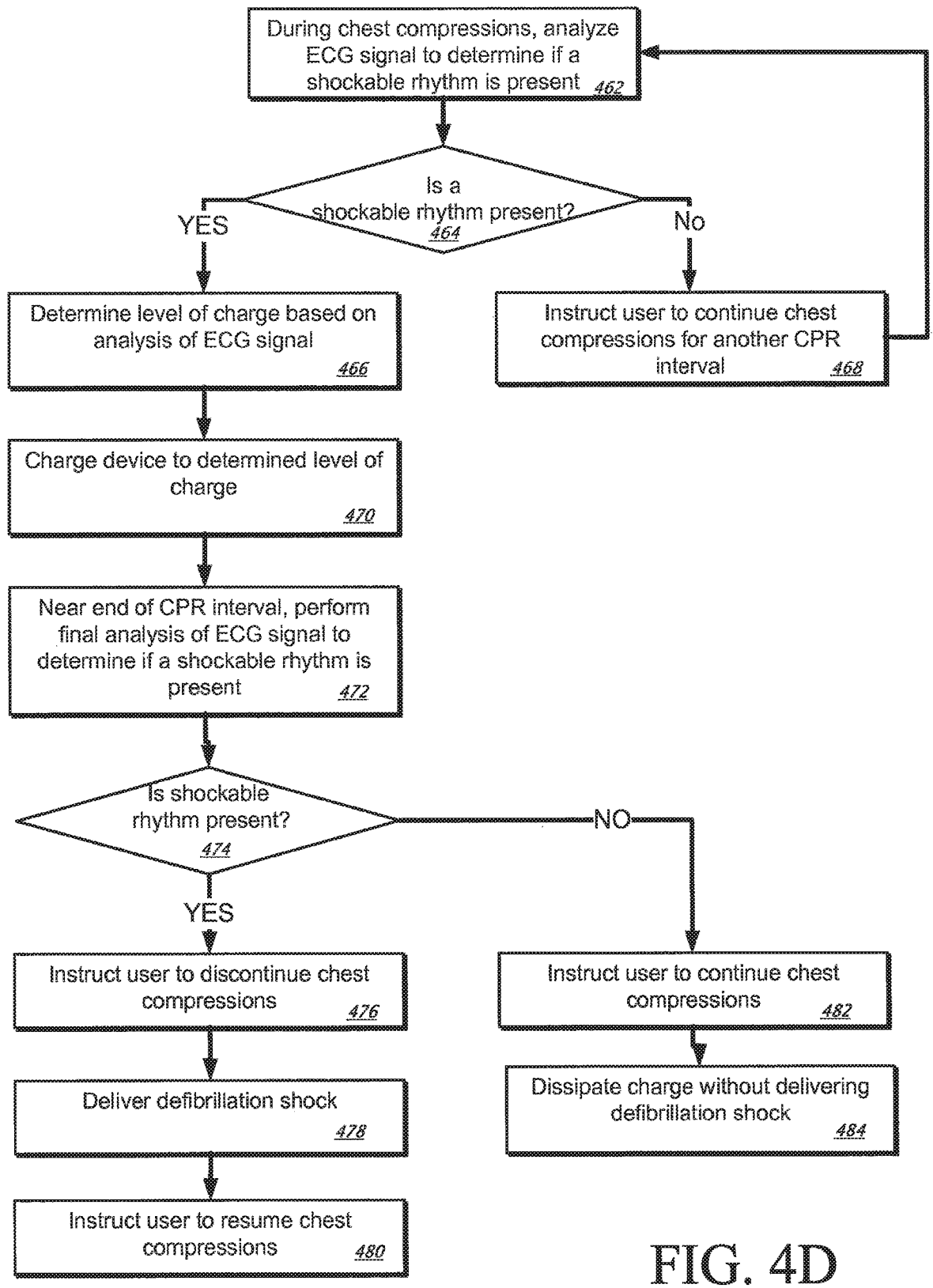
FIG. 4D is a flow chart showing actions taken to adaptively charge a defibrillation device to a level selected based on ECG analysis.

FIG. 4D is a flow chart showing actions taken to adaptively charge a defibrillation device to a level (e.g., a desired total voltage or charge) selected based on ECG analysis. For example, a level of charge for the defibrillation device (and a total amount of charge delivered to the victim) can be adaptively determined based on factors related to the ECG analysis such as the amplitude, frequency of the ECG signal, and/or an AMSA value. For example, if a victim is experiencing VF with a high amplitude ECG signal, only a low level of energy in the shock may be used. In contrast, in situations where it is not likely that conversion to a perfusing rhythm will occur with only a low energy shock such as situations in which the ECG signal exhibits a low amplitude, then the defibrillation device can be charged to a higher energy level.

In some implementations, an amplitude magnitude spectrum area (AMSA) value can be used to determine how to charge the defibrillation device and when to administer a defibrillation shock. For example, a high AMSA value is believed to be correlated to a high likelihood of conversion to a perfusing rhythm. The AMSA value can be monitored and the level of shock and/or length of time chest compressions are administered can be modified based on a threshold AMSA value and/or trends observed in the AMSA value. For example, a shock could be administered when a change (e.g., a decrease) in the AMSA value is observed by systems provided in an AED device. The AMSA value can also be used to determine the rate in charging the defibrillator. For example, an AMSA number that is associated with an accuracy level of 70% or greater (e.g., 70%, 80%, 90%) in predicting a successful conversion can be associated with the fastest possible rate in charging the defibrillator; The lower value the AMSA number is, the rate of charging is set to (e.g., half speed in charging when an AMSA number associated with an accuracy level of 50% is observed).

In FIG. 4D at block 462, while chest compressions are being administered, the AED device analyzes an ECG signal, and at box 464, the AED device determines if a shockable rhythm is likely to be present in the victim at the end of the CPR interval. If a shockable rhythm is not likely to be present in the victim at the end of the CPR interval, the AED instructs the rescuer to continue chest compressions for another CPR interval at box 468 and continues to receive and analyze the ECG signals. If the system determines that a shockable rhythm is likely to exist, at box 466, the AED device determines a level of charge based on an analysis of the ECG signal. For example, the level of charge or the rate of charging can be based on an amplitude of the ECG signal, a frequency of the ECG signal, and/or and AMSA value of the ECG signal. The level of charge can vary from a low charge to a high charge. In general, if the AMSA value is used, the level of charge is proportional to the AMSA value such that the device is charged to a higher level if the AMSA value is higher. At box 470, the AED charges the defibrillation device to the determined level of charge. The rate of charging can also vary from a slow charging rate to a fast charging rate: for example, if the AMSA value is used, the charging rate can be proportional to the AMSA value such that the device is charged faster if the AMSA value is higher.

Alternatively, other measures of the underlying energy status or perfusion state of physiologic tissue (ESPPT) of the victim may be utilized instead of AMSA is just described. These alternative measures of ESPPT may include near-infrared spectroscopy that has been shown to be able to measure tissue pH as well as mitochondrial energy status. Alternative ESPPT sensors may include fiber optic pO2 and pCO2 sensors such as that described by Cajlakovic and colleagues in "Simultaneously monitoring of tissue O2 and CO2 partial pressures by means of miniaturized implanted fiber optical sensors" (IEEE Sensors 2009 Conference). Location for sensing ESPPT is preferably in the buccal cavity, which has been shown in previous research for traumatic arrest, shock and cardiac arrest to provide good correlation to vital organ physiologic status. Other locations may be the tragus of the ear, intravenously either arterial or venous, or via fiberoptic needle probe into skeletal muscle tissue.

At box 472, near the end of the CPR interval, the AED device performs a final analysis and determines (box 474) if a shockable rhythm is present. If a shockable rhythm does not exist, the AED instructs the rescuer to continue chest compressions at box 482 such that the victim receives uninterrupted chest compressions. At box 483, the AED dissipates the charge (e.g., using one or more of the methods described herein) from the defibrillation device without delivering a shock to the victim.

If a shockable rhythm is observed, at box 476, the AED instructs the rescuer to discontinue chest compressions (e.g., using one or more of the methods described herein). At box 478, the AED device delivers the shock and at box 480, the AED device instructs the user to resume chest compressions.

Other data besides ECG data may be included as part of the determination of whether a shockable rhythm exists and may be incorporated into the analysis algorithm, for instance pulse oximetry, capnography, respiration, impedance cardiography, and blood pressure measurements. At least some of the data may remain in the time domain without any Fourier or other transform method being performed on it. Pulse oximetry, impedance cardiography, and blood pressure measurements may be used to augment the ECG to determine if a pulse is present. Capnography may be used to determine the overall effectiveness of cardiopulmonary resuscitation. The additional measures can also include measurement of velocity or acceleration of chest compression during chest compressions according to the techniques taught by U.S. Pat. No. 7,220,335, Method and Apparatus for Enhancement of Chest Compressions During Chest Compressions, the contents of which are hereby incorporated by reference in their entirety and U.S. patent application Ser. No. 11/430,579 titled ECG rhythm advisory method the contents of which are hereby incorporated by reference in their entirety.

In some embodiments, the cross-correlation between the ECG signal (with CPR artifact) and the CPR signal (in the form of compression acceleration, velocity, or displacement) can be calculated. Based on the strength of the cross-correlation between the ECG signal and the CPR signal, the system can select an appropriate analysis method to remove the artifacts from the ECG signal and determining if a shockable rhythm exists in the ECG signal. For example, a high cross-correlation value between the ECG signal and the CPR signal indicates that the majority of the artifact is from the chest compression and thus an analysis method designed for ECG with CPR artifact may be more reliable than other analysis methods. Alternatively, a low cross-correlation value typically indicates that there is strong non-CPR-related artifact in the recorded ECG signal.

Figures 5A, 5B:
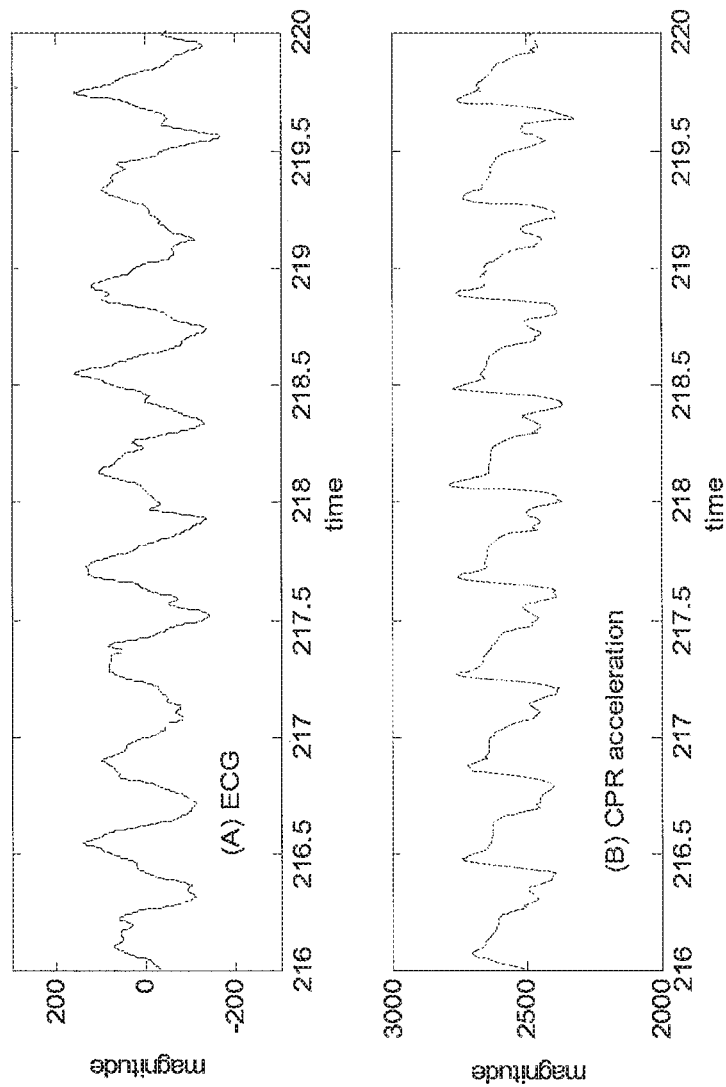
FIG. 5A is a diagram of and ECG signal.
FIG. 5B is a diagram of a CPR acceleration signal showing strong cross-correlation with the ECG signal.

FIGS. 5A and 5B illustrate an example of the observed ECG signal (FIG. 5A) showing strong cross-correlation with the CPR acceleration signal (FIG. 5A), which indicates that the ECG signal is free from non-CPR noise. The strong cross correlation can be observed based on the similarity in the shape of the CPR signal and the ECG signal. The cross correlation can be computed automatically during the analysis of the ECG signal.

Figure 6A:
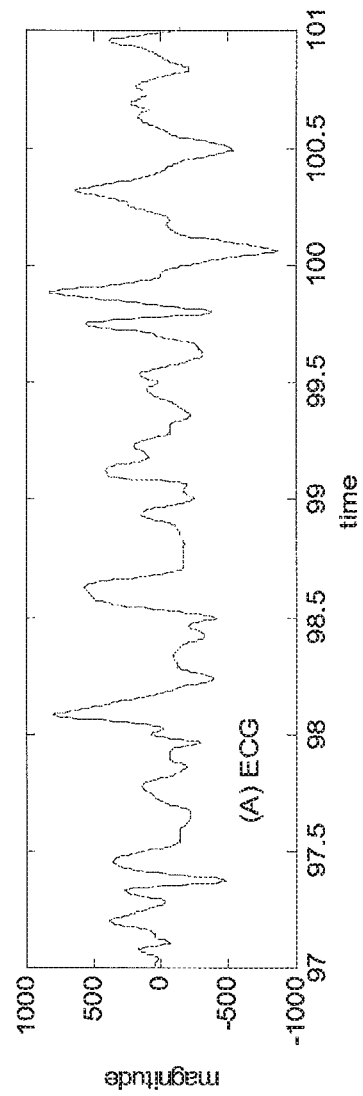
FIG. 6A is a diagram of and ECG signal.
Figure 6B:
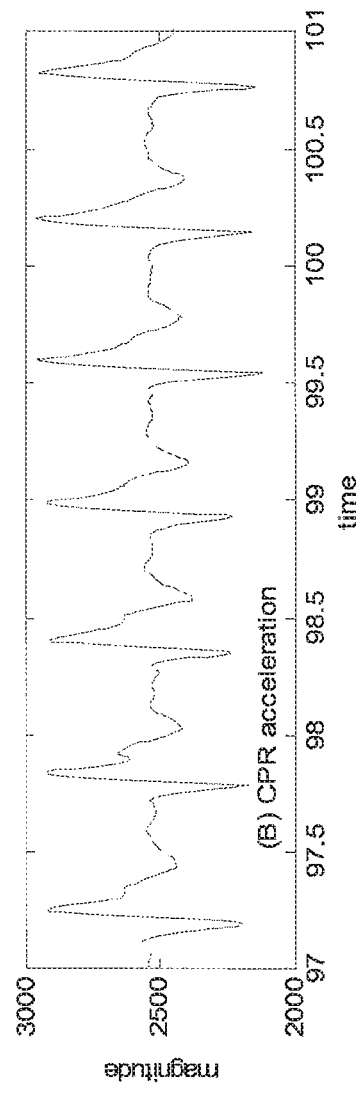
FIG. 6B is a diagram of a CPR acceleration signal showing low cross-correlation with the ECG signal.

As noted above, a low cross-correlation value between the ECG signal and the CPR signal typically indicates that there is strong non-CPR-related artifact in the recorded ECG signal. With the presence of the non-CPR-related artifact, the ECG analysis performed during CPR may be less reliable (or may not be reliable). Due to the lesser reliability of the ECG analysis, the system can utilize a longer period of CPR-free time in a re-confirmation analysis (e.g., a longer analysis period can be utilized after the cessation of CPR and prior to the determination of whether a shockable rhythm exists). FIGS. 6A and 6B illustrate an example of the observed ECG signal (FIG. 6A) with weak cross-correlation with the CPR acceleration signal (FIG. 6B). This indicates that the ECG has strong non-CPR noise and a longer of re-confirmation analysis period can be used.

The information processing technique can include but is not limited to simple combining rules or math, neural networks, expert systems incorporating fuzzy or standard logic, or other artificial intelligence techniques. For example, multiple factors can be combined to make a determination of whether to defibrillate. In some situations, even if a shockable rhythm exists (e.g., as determined based on the ECG analysis) the AED device may not recommend delivering the shock to the patient because one or more other factors suggest that another treatment would likely be more effective. For example, if a shockable rhythm exists but the quality of CPR chest compressions as measured based on one or more of the velocity, acceleration, or depth of the compressions is low, then the AED device could recommend continuing chest compressions to increase blood circulation rather than stopping the chest compressions to deliver the shock.

In some embodiments, the AED device can combine different measures and output results related to the desirability of defibrillation and/or the effectiveness of the chest compressions being delivered by the rescuer. Exemplary outputs can include statements such as "strong need for defibrillation," "weak need for defibrillation," "faster chest compressions needed," or "additional chest compressions needed."

In some embodiments, the AED device can deliver the defibrillation shock during the chest compression cycle (e.g., while the rescuer is delivering the chest compressions). For example, the AED can synchronize of the defibrillation shock to the chest compression cycle. Delivery of the defibrillation shock during the early portion (approximately the first 300 milliseconds) of the decompression (diastolic) phase of the chest compression cycle can improve the likelihood of success of the delivered shock. The decompression phase begins when the rescuer reduces compression force on the chest, allowing the chest to rise, and the heart to expand. The AED device can detect chest compression phase and timing information indicative of the start of the decompression phase and initiate delivery of the electromagnetic therapy within 300 milliseconds of the start of the decompression phase. In some embodiments, delivery of electromagnetic therapy can be initiated within 25-250 milliseconds of the start of the decompression phase. Circuitry and processing for the detection of chest compression phase timing information can include a pressure sensor and/or an accelerometer. Exemplary methods for synchronizing defibrillation with chest compression phase are described in U.S. patent application Ser. 12/263,813 titled Synchronization of Defibrillation and Chest Compressions, the contents of which are hereby incorporated by reference in their entirety.

Large self-adhesive electrode pads (~5" in diameter) are typically used to deliver defibrillation therapy to patients. The pads also provide ECG monitoring through the conductive surfaces that deliver therapy. In one implementation, additional small (~0.5" diameter) ECG electrodes can be integrated into the large pads.

In one embodiment, the two small ECG electrodes and large pads are configured such that there at least two mutually orthogonal ECG leads are generated. The vector sum of these leads generates a trajectory over time. The same methods for trajectory analysis described above may be used to analyze this trajectory as well.

Additionally, the defibrillator may take the form of a wearable defibrillator such as the LifeVest, manufactured by ZOLL Medical (Chelmsford, Mass.).

Many other implementations other than those described may be employed, and may be encompassed by the following claims.

What is claimed is:

1. An external defibrillator comprising:
a processor;
a defibrillator pulse generator operatively connected to the processor and configured to generate a defibrillating shock; and
electrode pads configured to be operatively connected to the defibrillator pulse generator and the processor to deliver the defibrillating shock from the defibrillator pulse generator to the patient, the electrode pads further configured to deliver one or more ECG signals from the patient to the processor,
wherein the processor is programmed to:
analyze one or more electrocardiogram (ECG) signals from the patient during delivery of chest compressions to the patient;
determine appropriateness of delivering a shock to the patient based on the analysis of the one or more ECG signals during the delivery of chest compressions of a CPR interval;
determine that the chest compressions of the CPR interval have been completed;
analyze one or more ECG signals acquired in an absence of chest compressions within about 5 seconds after cessation of the chest compressions of the CPR interval to confirm the appropriateness of delivering the shock to the patient; and
provide an indication on a display screen of a recommendation of providing a shock to the patient based on the determined appropriateness of delivering the shock to the patient.

2. The external defibrillator of claim 1, wherein the processor is programmed to provide the indication on the display screen of the recommendation of providing the shock to the patient based on the confirmed appropriateness of delivering the shock to the patient from the analysis of the one or more ECG signals acquired in the absence of chest compressions.

3. The external defibrillator of claim 1, wherein the analysis of the one or more ECG signals acquired in an absence of chest compressions occurs within about 3 seconds after the cessation of the chest compressions of the CPR interval.

4. The external defibrillator of claim 1, wherein the analysis of the one or more ECG signals acquired in an absence of chest compressions occurs within about 1 second after the cessation of the chest compressions of the CPR interval.

5. The external defibrillator of claim 1, wherein a duration of the CPR interval is preset in the processor.

6. The external defibrillator of claim 5, wherein the duration of the CPR interval is about two minutes.

7. The external defibrillator of claim 1, wherein the processor is programmed to provide instructions to cease chest compressions once the CPR interval has been completed.

8. The external defibrillator of claim 7, wherein the instructions comprise an output for a rescuer to cease manual compressions once the CPR interval has been completed.

9. The external defibrillator of claim 1, wherein the defibrillator pulse generator comprises a capacitor electrically connected to an electrical energy storage source.

10. The external defibrillator of claim 9, wherein the processor is programmed to charge the capacitor during delivery of the chest compressions of the CPR interval to the patient.

11. The external defibrillator of claim 9, further comprising one or more safety interlocks to prevent accidental discharge of the capacitor during charging of the capacitor.

12. The external defibrillator of claim 9, wherein the processor is programmed to cause the capacitor to dissipate a charge if the analysis of the one or more ECG signals acquired in the absence of chest compressions does not confirm the appropriateness of delivering the shock to the patient.

13. The external defibrillator of claim 9, wherein the processor is programmed to, based on the analysis of the one or more ECG signals, determine whether to charge the capacitor or to provide instructions to continue the chest compressions of the CPR interval without charging the capacitor.

14. The external defibrillator of claim 9, wherein the processor is programmed to, based on the analysis of the one or more ECG signals, determine whether to provide instructions to continue the chest compressions of the CPR interval.

15. The external defibrillator of claim 1, wherein the electrode pads comprise adhesive material for adhering to the patient.

16. The external defibrillator of claim 1, wherein determining the appropriateness of delivering the shock to the patient during delivery of the chest compressions of the CPR interval to the patient comprises determining a level of certainty of whether the shock is appropriate, the level of certainty being one of at least a low level of certainty and a high level of certainty.

17. The external defibrillator of claim 16, wherein the processor is configured to provide the indication of the recommendation of providing the shock to the patient immediately after cessation of chest compressions when reaching a high enough level of certainty of appropriateness of delivering the shock.

18. The external defibrillator of claim 16, wherein the processor is configured to confirm the appropriateness of delivering the shock to the patient based on the analysis of the one or more ECG signals acquired in the absence of chest compressions when the level of certainty of appropriateness of delivering the shock is insufficient.

19. The external defibrillator of claim 1, wherein a duration of the CPR interval is variable based on analysis of the one or more ECG signals by the processor.

20. The external defibrillator of claim 1, wherein the processor is further programmed to control the defibrillator pulse generator to deliver the shock to the patient based at least in part on the confirmation of the appropriateness of delivering the shock to the patient.

21. The external defibrillator of claim 1, further comprising a therapy button configured to cause the defibrillator pulse generator to deliver the defibrillating shock to the patient.

22. The external defibrillator of claim 21, further comprising a safety interlock for controlling enablement of the therapy button that causes the defibrillator pulse generator to deliver the defibrillating shock to the patient.

23. The external defibrillator of claim 22, wherein the processor is programmed to disable the safety interlock so as to enable the therapy button to cause the defibrillator pulse generator to deliver the defibrillating shock to the patient.

24. The external defibrillator of claim 23, wherein the processor is programmed to disable the safety interlock based on the confirmed appropriateness of delivering the shock to the patient.

25. The external defibrillator of claim 1, further comprising:
   circuitry for detection of chest compressions delivered to the patient.

26. The external defibrillator of claim 25, wherein the processor is programmed to determine that the chest compressions of the CPR interval have been completed based on a signal from the circuitry for detection of chest compressions delivered to the patient.

27. A method for providing electrical therapy to a patient, the method comprising:
   analyzing one or more electrocardiogram (ECG) signals from the patient during delivery of chest compressions of a CPR interval to the patient;
   determining appropriateness of delivering a shock to the patient based on the analysis of the one or more ECG signals during the delivery of the chest compressions;
   determining that chest compressions of the CPR interval have been completed;
   after the chest compressions of the CPR interval have been completed, analyzing one or more ECG signals to confirm the appropriateness of delivering the shock to the patient within about 5 seconds after a rescuer has completed the chest compressions of the CPR interval; and
   providing an indication on a display device of a recommendation of providing a shock to the patient based on the determined appropriateness of delivering the shock to the patient.

28. The method of claim 27, further comprising setting a duration of the CPR interval.

29. The method of claim 28, wherein the duration of the CPR interval is preset.

30. The method of claim 29, wherein the duration of the CPR interval is about two minutes.

31. The method of claim 27, further comprising providing an indication to the rescuer that the CPR interval is completed.

* * * * *